US010869680B2

(12) United States Patent
Marionneaux et al.

(10) Patent No.: US 10,869,680 B2
(45) Date of Patent: Dec. 22, 2020

(54) POSITIONING BRACKET FOR MULTIPLE BONE TUNNEL DRILL GUIDES

(71) Applicant: CLEMSON UNIVERSITY, Clemson, SC (US)

(72) Inventors: Alan Michael Marionneaux, Greenville, SC (US); Michael David Stokes, Simpsonville, SC (US); George Marion Seignious, IV, Mt. Pleasant, SC (US); Alison Santillo, Ponte Vedra Beach, FL (US); Jeremy Mercuri, Piedmont, SC (US); Nicholas Freeman, Ponte Vedra Beach, FL (US); Adam Marrocco, Central, SC (US); Steven Brian Singleton, Vail, CO (US); Brian Curtis Keim, Landrum, SC (US)

(73) Assignee: Clemson University, Clemson, SC (US)

( * ) Notice: Subject to any disclaimer, the term of this patent is extended or adjusted under 35 U.S.C. 154(b) by 935 days.

(21) Appl. No.: 15/046,697

(22) Filed: Feb. 18, 2016

(65) Prior Publication Data
US 2016/0235421 A1 Aug. 18, 2016

Related U.S. Application Data (60) Provisional application No. 62/117,666, filed on Feb. 18, 2015.

(51) Int. Cl.
*A61B 17/17* (2006.01)

(52) U.S. Cl.
CPC ...... *A61B 17/1764* (2013.01); *A61B 17/1714* (2013.01); *A61B 17/1757* (2013.01); *A61B 17/1778* (2016.11)

(58) Field of Classification Search
CPC . A61B 17/17; A61B 17/1703; A61B 17/1717; A61B 17/1721; A61B 17/1725; A61B 17/1728; A61B 17/1732
See application file for complete search history.

(56) References Cited

U.S. PATENT DOCUMENTS

| 2,991,096 | A |   | 7/1961  | Davidson |
| 3,221,743 | A | * | 12/1965 | Thompson ............. A61G 13/12 606/1 |
| 3,662,618 | A |   | 5/1972  | Kroll et al. |
| 4,483,334 | A | * | 11/1984 | Murray .................. A61B 17/60 403/391 |
| 4,600,006 | A | * | 7/1986  | Baker ................ A61B 17/1695 408/139 |

(Continued)

OTHER PUBLICATIONS

Boutsiadis, MD, et al; "Arthroscopic 4-Point Suture Fixation of Anterior Cruciate Ligament Tibial Avulsion Fractures," *Arthroscopy Techniques,* Dec. 2014; vol. 3, No. 6, pp. e683-e687.

(Continued)

*Primary Examiner* — Anu Ramana
(74) *Attorney, Agent, or Firm* — Dority & Manning, P.A.

(57) ABSTRACT

A medical positioning bracket is described that provides users with the ability to attach and secure multiple bone tunnel drill guides into a single working unit. Users can manipulate each drill guide independently and lock the drill guides at desired locations relative to one another to achieve precise bone tunnel angles and locations.

17 Claims, 7 Drawing Sheets

(56) References Cited

U.S. PATENT DOCUMENTS

| | | | | |
|---|---|---|---|---|
| 4,672,957 | A | * | 6/1987 | Hourahane ........ A61B 17/1714 606/80 |
| 4,907,577 | A | * | 3/1990 | Wu .................... A61B 17/1757 606/104 |
| 5,160,335 | A | * | 11/1992 | Wagenknecht .... A61B 17/6466 606/57 |
| 5,207,676 | A | * | 5/1993 | Canadell ............ A61B 17/6491 606/54 |
| 5,573,538 | A | | 11/1996 | Laboureau |
| 5,888,197 | A | * | 3/1999 | Mulac .................... A61B 17/02 403/396 |
| 6,017,306 | A | * | 1/2000 | Bigliani ................. A61B 17/02 600/227 |
| 6,379,364 | B1 | | 4/2002 | Brace et al. |
| 6,616,664 | B2 | * | 9/2003 | Walulik ............... A61B 17/645 600/230 |
| 7,125,380 | B2 | * | 10/2006 | Yager ................. A61B 17/0293 600/227 |
| 7,338,442 | B2 | * | 3/2008 | Mulac .................... A61B 17/02 600/226 |
| 7,758,582 | B2 | * | 7/2010 | Ferrante ............. A61B 17/6466 606/96 |
| 7,842,042 | B2 | | 11/2010 | Reay-Young et al. |
| 8,551,123 | B2 | | 10/2013 | Pandya |
| 8,685,033 | B2 | | 4/2014 | Johnson et al. |
| 8,771,282 | B2 | | 7/2014 | Blain et al. |
| 8,821,491 | B2 | * | 9/2014 | Chreene ............. A61B 17/6466 606/59 |
| 8,986,314 | B1 | * | 3/2015 | Jordan ............... A61B 17/1714 606/96 |
| 8,986,316 | B1 | * | 3/2015 | Jordan ............... A61B 17/1714 606/96 |
| 2002/0026190 | A1 | * | 2/2002 | Walulik ............... A61B 17/645 606/57 |
| 2003/0199738 | A1 | * | 10/2003 | Yager ................. A61B 17/0293 600/227 |
| 2008/0103506 | A1 | | 5/2008 | Volpi et al. |
| 2010/0191247 | A1 | | 7/2010 | Schneider |
| 2013/0325011 | A1 | | 12/2013 | Cleveland et al. |

OTHER PUBLICATIONS

Leeberg, et al.; "Tibial eminentia avulsion fracture in children—a systematic review of the current literature," *Dan Med J.* (2014) 61(3) pp. 1-7.

Lubowitz; "Anterior Cruciate Ligament Tibial Guide Pin Accuracy and Surgical Precision: Comparing 3.0FMm and 2.4Fmm Guide Pins," *Journal of Arthroscopie and Related Surgery* (2010) 26(4) pp. 500-505.

O'Brien, et al.; "Orthopedic Outlook," Chicago, 2011. (1 page).

Penny; "Arthroscopic Fixation of Tibial Spine Fractures," *Techniques in Knee Surgery*, (*Lippincog Williams & Wilkins*) (2007), 7 pages.

Verdano, et al.; "Arthroscopic absoprbable suture fixatiuon for tibial spine franctures," *Arthroscopy Techniques* (2013) 3(1) pp. 45-48.

Wood; "Sports Medicine—Global Analysis and Market Forecasts," 2014-2020, (2014) 3 pages.

Arthrex. "Ankle Arthroscopy" https://www.arthrex.com/foot-ankle/ankle-arthroscopy.

Arthroscopy Association of North America. "Frequently Used Codes" (2014) (Restricted Web).

Centers for Medicare and Medicaid Services. "ICD-9 Codes Including in Range 823.00-824.9" (2014) (Web).

Cooper L.M. "Second Fracture and Tibial Spine Avulsion Fracture Secondary to Sporting Injury" *Euro Soc Rad* (2009).

Everything About Achilles Tendons. "Types of Achilles Tendon Injuries" (2014).

Johnson & Johnson. Annual Report (2013).

Kendall, et al. "Fracture of the Tibial Spine in Adults and Children" *J Bone Joint Surg* (1992) pp. 844-852.

Macario A. "What does one minute of operating room time cost?" *J Clin Anesth* 22 (2010) pp. 1-4.

Shippert, R. "A study of time-dependent operating room fees and how to save $100,000 by using time-saving products." *Am J. Cosm Surg* 22(1) p. 25-34. (Abstract only).

Smith & Nephew. Annual Report (2013).

Thomson Reuters. "Research Report: U.S. Market for Arthroscopic Devices" *Research and Markets* (2014).

U.S. Food & Drug Administration. "Device Advice: Comprehensive Regulatory Assistance" http://www.fda.gov/MedicalDevices/DeviceRegualtionand Guidance/Overview/ClassifyYourDevice/ucm051549.htm.

U.S. Food & Drug Administration. "Medical Device Exemptions 510(k) and GMP Requirements" https://ww.accessdata.fda.gov/scripts/cdrh/cfdocs/cfpcd/315.cfm Yamaguchi, K. "New Guideline on Rotator Cuff Problems" *Am Soc Ortho Surg* 5(1) (2011) pp. 46-47. (Abstract only).

\* cited by examiner

POSITIONING BRACKET FOR MULTIPLE BONE TUNNEL DRILL GUIDES

CROSS REFERENCE TO RELATED APPLICATION

This application claims filing benefit of U.S. Provisional Patent Application Ser. No. 62/117,666 entitled "Conventus" having a filing date of Feb. 18, 2015, which is incorporated herein by reference for all purposes.

STATEMENT AS TO RIGHTS TO INVENTIONS MADE UNDER FEDERALLY SPONSORED RESEARCH

This invention was made with Government support under EB016589 awarded by The National Institutes of Health. The Government has certain rights in the invention.

BACKGROUND

Each year hundreds of thousands of orthopedic surgeries are performed in the United States that require fixation of hard or soft tissue to underlying bone. For these procedures, a screw-based repair method is often selected for its speed and ease of use despite disadvantages that include an estimated 43% revision rate.

Studies have indicated that suture-based repair methods offer significantly improved clinical outcomes, but these methods are time consuming and technically difficult as suture-based repair methods require drilling of multiple bone tunnels for tissue fixation. The tunnels are formed by use of a bone tunnel drill guide that is repositioned prior to the drilling of each tunnel. Displacement of tissue and bone tunnel misalignment often occurs during such repair methods due to the sequential repositioning of the bone tunnel drill guide for each bone tunnel to be formed.

There are existing drill guides that have multiple bores allowing for drilling of multiple bone tunnels at a single position, however, these devices offer only the tunnel angles and separation distances as set by the characteristics of the device; there is no adjustment capability. There are currently no bone tunnel drill guide devices that allow for surgeons to simultaneously adjust multiple different drill guides to a range of tunnel orientations and locations.

Accordingly, what is needed in the art is a device that allows for accurate and independent placement of multiple bone tunnel drill guides simultaneously. Such a device would decrease the likelihood of mislocation and misalignment of bone tunnels in procedures such as suture-based orthopedic repair. In addition, such a device could reduce time spent and therefore costs incurred in surgical time as well as decrease potential revision following surgery.

SUMMARY

Aspects and advantages of the invention will be set forth in part in the following description, or may be obvious from the description, or may be learned through practice of the invention.

According to one embodiment, a positioning bracket for use in conjunction with multiple bone tunnel drill guides is disclosed. The positioning bracket can include a frame, first and second slide blocks slidably attached to the frame, and first and second adapter blocks that are attachable to the frame via the first and second slide blocks, respectively.

The first and second slide blocks can be attached to the frame and independently capable of motion across the frame in a lateral direction. The slide blocks can each also include a locking mechanism that is engagable with the frame so as to be capable of being locked in place at a desired location on the frame. As such, the adapter blocks that are attached to the frame via the slide blocks can be moved relative to one another and then locked in place at a predetermined location with respect to one another.

According to one embodiment, one or both of the adapter blocks can also be mounted with the slide blocks in such a fashion so as to be rotatable about an axis. In another embodiment, one or both of the adapter blocks can be rotatable about multiple axes. Accordingly, the adapter blocks can exhibit a single or multiple degrees of freedom.

Also disclosed are methods for using the positioning bracket to properly locate multiple bone tunnel drill guides with respect to one another and with respect to a patient. For instance, during use, a first bone tunnel drill guide can be removably attached to the first adapter block and a second bone tunnel drill guide can be removably attached to the second adapter block. The bone tunnel drill guides can then be locked in place on the positioning bracket relative to one another as desired by the surgeon, and each bone tunnel drill guide can then be used according to known methodology to guide the surgeon during the formation of a bone tunnel. By locking the bone tunnel drill guides in the desired orientation relative to one another followed by proper location on the patient, multiple bone tunnels can be formed with a high degree of accuracy in alignment and orientation.

These and other features, aspects and advantages of the present disclosure will become better understood with reference to the following description and appended claims.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

DETAILED DESCRIPTION

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to a medical positioning bracket that provides users with the ability to attach and secure multiple bone tunnel drill guides into one efficient working unit. Users can manipulate each drill guide independently and lock the drill guides at desired locations and orientations relative to one another to achieve precise tunnel angles and separation distances without repositioning of the drill guides during a procedure. Through simultaneous stabilization of all bone tunnel drill guides necessary for a procedure with a single positioning bracket, sequential formation of the multiple bone tunnels can be carried out without disturbing repaired tissue, which is a common problem when sequentially locating a single drill guide to form multiple bone tunnels. The drill guide stability provided by the system can improve the ability of a surgeon to maintain the alignment of the entire system during a procedure. Moreover, the simultaneous stabilization of multiple bone tunnel drill guides can improve accuracy of the alignment of the formed bone tunnels.

Beneficially, the positioning bracket can be utilized in conjunction with any off the-shelf drill guides to provide an adjustable, multi-drill guide system for use in arthroscopic tissue fixation. By use of the device, surgeons can efficiently adjust and secure each drill guide independently to provide the necessary separation distances and tunnel angles and accurately drill multiple bone tunnels. This can provide a route for the surgeon to quickly drill multiple bone tunnels and thereby minimize surgical time and frustration as less time and effort need be spent aligning and drilling the tunnels. Use of the device can decrease surgical time and procedural difficulty. While the device design does not restrict or limit a surgeon's method of suture fixation, in one embodiment use of the device can make suture-based bone fixation methods more accessible to surgeons. Overall, use of the device can improve clinical outcomes of orthopedic procedures.

The adjustability of the device means that the device can be utilized to meet precise tunnel angles and distances between bone tunnels. Thus, the device is adaptable to meet a wide range of both procedure- and patient-based requirements and is suitable for use in multiple types of surgeries. Disclosed devices can be utilized for a number of tissue attachment surgeries including, and without limitation, rotator cuff repair, tibial spine avulsion/ACL/PCL reattachment, and Achilles tendon repair.

Figure 1:
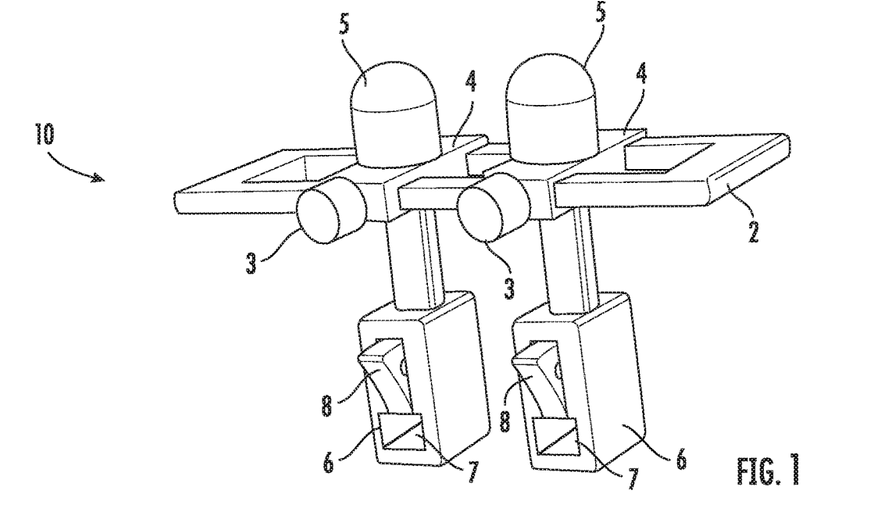
FIG. 1 illustrates a perspective view of one embodiment of a positioning bracket.
Figure 2:
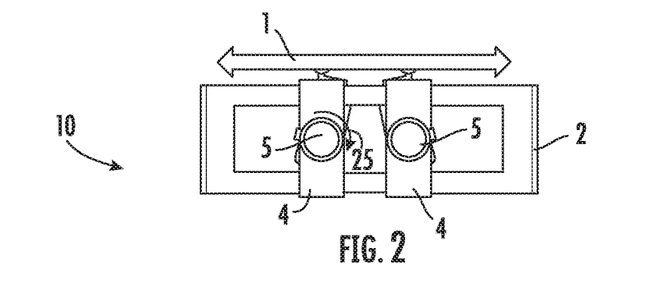
FIG. 2 illustrates a top view of a positioning bracket.

Referring to FIG. 1 and FIG. 2, one embodiment of a positioning bracket 10 is illustrated. The positioning bracket 10 includes a frame 2, two slide blocks 4, and two adapter blocks 6. A slide block assembly including a slide block 4 and an associated adapter block 6 is more clearly illustrated in FIG. 3A, FIG. 3B, and FIG. 3C. Each adapter block 6 can carry a bone tunnel drill guide. For instance, an end of a bone tunnel drill guide 28 (FIG. 3A) can be held in a recess 7 by use of a locking block 8 retained by associated hardware 9. A bone tunnel drill guide can thus be retained by the positioning bracket without interfering with the drill guide operation.

Though illustrated as carrying two adapter blocks 6, it should be understood that a positioning bracket is not limited to securing only to adapter blocks, and additional adapter blocks can be incorporated in a device, each of which capable of carrying bone tunnel drill guides or other surgical devices for use in a procedure.

As illustrated in FIG. 2, a positioning bracket 10 can allow for motion of the slide blocks 4 in a lateral direction as indicated by the directional arrow 1. Thus, the distance between the slide blocks 4 can be controlled. As illustrated in FIG. 1 and FIG. 3A-3C, each of the slide blocks 4 can also include a locking mechanism such as a setscrew 3 or the like, that can lock each individual slide block 4 in place on the frame 2. Thus, the distance between the slide blocks 4 and the associated adapter blocks 6 can be fixed.

A device can also allow for rotation of the adapter blocks 6 in one or more degrees of freedom. For example, a positioning bracket 10 can include a cap 5 at the end of the shaft 11 of the adapter block 6 that can hold the adapter block 6 in place and can allow for rotation of the adapter blocks 6 about the axis of the shaft 11 as indicated by the directional arrow 25 in FIG. 2. For instance, slotted locking collar 12, setscrew 13, and bolt 14 can together allow for rotation of the shaft 11 as the cap 5 is turned and subsequent locking of the shaft 11 at the desired angular rotation of the adapter block.

In one embodiment, the positioning bracket can be capable of disassembly through removal of the various screws, pins, blocks, etc., allowing for complete disassembly and sterilization. The various components of a positioning block can be formed of suitable materials as are generally known in the art and are capable of sterilization including, without limitation, various grades of stainless steel, carbon steel, aluminum alloys, etc. The various components can be formed of the same materials as one another or of different materials, as desired, and can generally be formed according to standard formation and machining methodology.

FIG. 4A-FIG. 4D present views of one embodiment of a frame 2 as may be incorporated in a positioning block. As illustrated, in this embodiment, a frame 2 can have a rectangular shape that can include two longer legs 20, 21 and two shorter ends 22, 23. The longer legs 20, 21 can be slidably engaged with the slide blocks 4 (FIG. 1).

The frame 2 can be strong enough so as to withstand all forces that will occur during surgery without substantial bending or deformation. For instance, a frame can bend in any direction by about 0.1 millimeter (mm) or less under expected surgical load conditions (e.g., about 11 Newtons (N) or less), or about 0.08 mm or less in some embodiments. For example, the maximum amount of bending of a frame can be in a worst case scenario of all expected weight of the slide block assemblies and associated drill guides being shifted to one end of the frame with the frame supported only at the other end.

FIG. 5A-FIG. 5D present various views of a slide block 4 as may be utilized in conjunction with a frame 2. As shown, slide block 4 is supported via two channels 30, 31 that can engage with legs 20, 21 of a frame 2. The slide block 4 is slidably connected to the frame 2 in either a permanent or removable fashion. For instance, a slide block 4 can be attached to a frame 2 via the channels 30, 31 during formation of the frame, in which case the frame can be completed following attachment of the slide block 4 thereto. Alternatively, an end or side of the frame 2 can be removably attached, in which case it may be possible to remove the slide block 4 from the frame 2 for cleaning, sterilizing, etc. and then reattachment for use.

The slide block 4 allows for drill guides secured in the positioning bracket to be moved laterally in relation to each other. Once the surgeon has decided on a lateral distance of separation for the drill guides that can be positioned by use of the device, the slide blocks 4 can be located on the frame 2 at the desired locations and locked into place. Any suitable locking mechanism can be utilized. For instance, in one embodiment, the locking mechanism can include a setscrew 3 (FIG. 1) that can apply suitable force to the frame 2 via access 32 such that it will be at most negligibly shifted during use.

A slide block 4 can include an aperture 33 for mounting of an adapter block 6 (FIG. 6A) as well as a setscrew access 32 or other suitable locking mechanism. Slide block 4 also includes a series of positional indentions 34 that can be mated with a peg 51 of an angle adjustment knob (FIG. 7D) for locking an adapter block at a desired rotational angle.

The slide block 4 and frame 2 can be sized so as to provide the desired adjustability to the positioning bracket. For instance, the slide block 4 can include positional indentations 34 in a full 360° at increments of about 5° or less, about 3° or less, or about 2° or less so as to provide wide variation in rotational location of an adapter block. In addition, the frame 2 can be large enough to allow for expected distance variability between drill guides. For instance, the frame 2 and slide blocks 4 can be sized such that the central axes of the apertures 33 can be about 100 mm apart, for instance from about 3 mm apart to about 90 mm apart, or from about 5 mm apart to about 25 mm apart in some embodiments. For example, tibial spine fracture repair according to a sutures-based repair method requires the formation of bone tunnels on either side of the reduced tibial spine. As a result of the variation in patient anatomy as well as variation in the method of injury, the tibial spine varies in width from case to case. In general, the width of a fractured tibial spine can be anywhere from about 3 mm to about 30 mm, with an average width of from about 10 mm to about 15 mm. A positioning bracket can include a frame and slide blocks sized so as to allow adjustment of the lateral distance between two drill guide tips held by the bracket so as to accurately straddle the tibial spine during surgery.

Figure 5A:
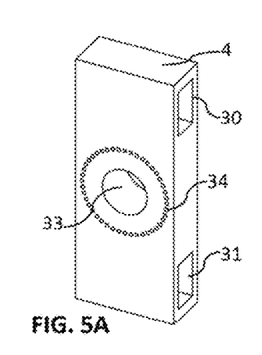
FIG. 5A illustrates a perspective view of a slide block of a positioning bracket.
Figure 5B:
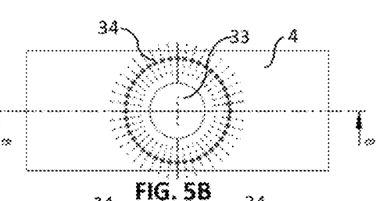
FIG. 5B is a front view of a slide block.
Figure 5C:
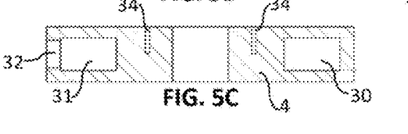
FIG. 5C is a first side view of a slide block.
Figure 5D:
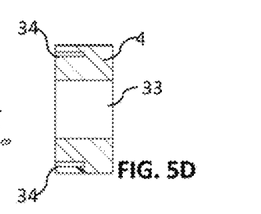
FIG. 5D is a second side view of a slide block.

The slide block 4 can be mounted via one or more attachments such as on the two legs 20, 21 of a frame 2 (FIG. 4B) via the channels 30, 31 as shown in FIG. 5A. Setscrews 3 tighten down onto the frame 2 (FIG. 1) via access 32 (FIG. 5C). Once tightened, the slide blocks 4 can be locked into place, preventing the adapter blocks and drill guides from moving during surgery. The slide blocks 4, when loosened via the setscrews 3, can be moved anywhere along the frame 2.

Figure 6A:
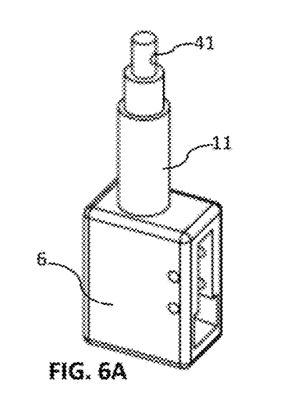
FIG. 6A illustrates a perspective view of an adapter block of a positioning bracket.
Figure 6B:
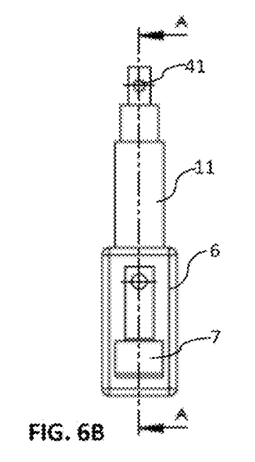
FIG. 6B is a first side view of an adapter block.
Figure 6C:
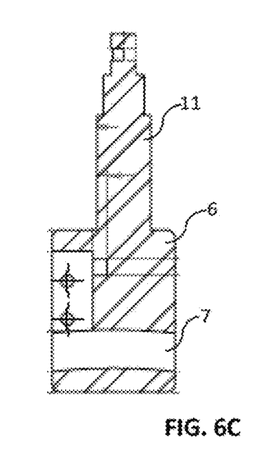
FIG. 6C is a second side view of an adapter block.

FIGS. 6A, 6B, and 6C present three views of one embodiment of an adapter block 6. The adapter block is the component that can hold a drill guide during use. The adapter block 6 includes a shaft 11 that can be used to connect the adapter block 6 to the frame 2 via a sliding block 4. The shaft 11 should be resilient enough so as to avoid bending under expected pressures of use so as to avoid misalignment of a drill guide used with the positioning bracket. For instance, the shaft 11 can withstand a force of about 50 N or less, for instance about 48 N, with negligible deflection.

Figure 3A:
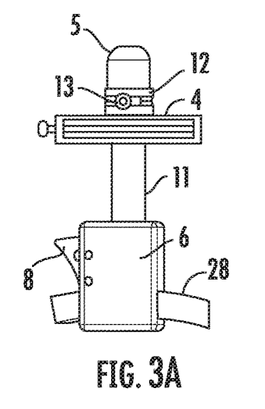
FIG. 3A illustrates a side view of a slider assembly of a positioning bracket.

In the embodiment of FIG. 6A-6C, the shaft 11 can vary in diameter, for instance with a step change in diameter at the location at which the shaft 11 will meet the slide block 4 upon assembly (FIG. 3A). This can prevent the adapter block 6 from excessive axial movement with the slide block 4. A positioning bracket can include a locking mechanism such as a setscrew 13 that meets with an indentation 41 in the shaft 11 of the adapter block 6 that can assist in locking the components of the device to one another.

In addition to the ability to adjust a lateral distance between drill guides retained by a positioning bracket, a system can also allow for the drill guides to be rotated with respect to one another in one or more degrees of freedom. For instance, the adapter blocks 6 of the positioning bracket 10 in FIG. 1 can be independently rotated around the axis of their respective shafts 11. This can allow drill guides held in the adapter blocks 6 to be oriented relative to one another at any desired angle.

Figure 3B:
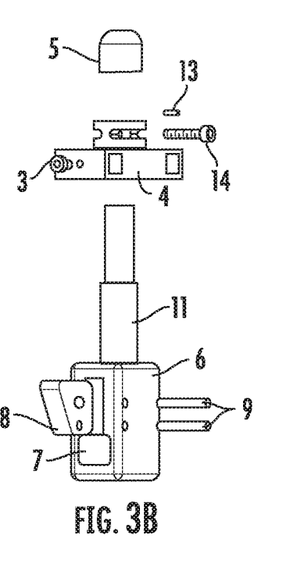
FIG. 3B illustrates a perspective exploded image of a slider assembly.
Figure 3C:
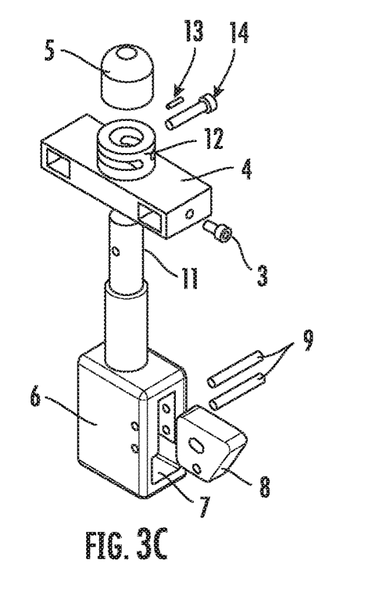
FIG. 3C illustrates a perspective exploded image of a slider assembly.
Figure 4A:
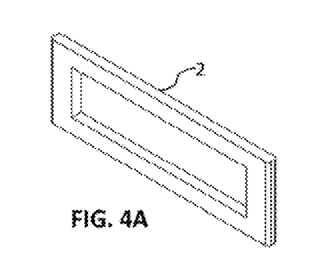
FIG. 4A illustrates a perspective view of a frame of a positioning bracket.
Figure 4B:
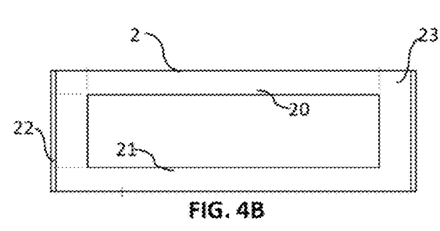
FIG. 4B is a front view of a frame.
Figure 4C:
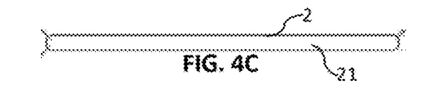
FIG. 4C is a first side view of a frame.
Figure 4D:
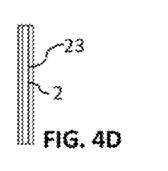
FIG. 4D is a second side view of a frame.
Figure 7A:
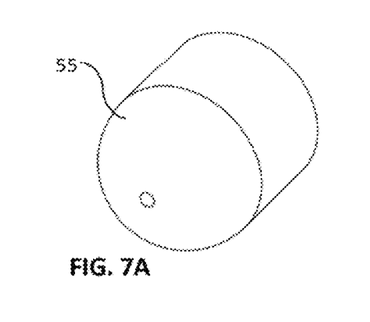
FIG. 7A illustrates a perspective view of an angle adjustment knob of a positioning bracket.
Figure 7B:
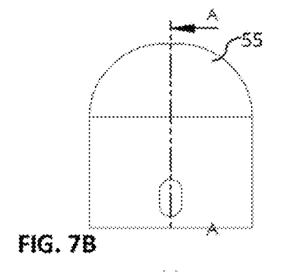
FIG. 7B is a first side view of an angle adjustment knob.
Figure 7C:
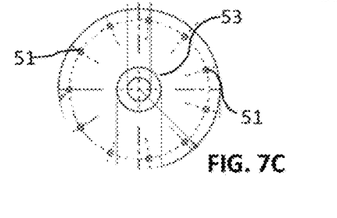
FIG. 7C is a top view of an angle adjustment knob.
Figure 7D:
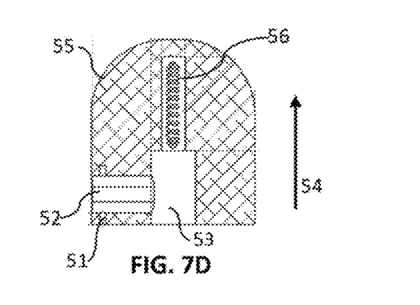
FIG. 7D is a second side view of an angle adjustment knob.

FIGS. 7A, 7B, 7C, and 7D illustrate various views of an angle adjustment knob 55 that can be utilized to hold and rotate an adapter block, e.g., adapter block 6 held in conjunction with slide block 4. This angle adjustment knob 55 of FIG. 7A-7D is similar to the angle adjustment knob 5 of FIGS. 3A, 3B, and 3C, but is of a unitary construction as opposed to including a separable slotted locking collar 12 as illustrated in the embodiment of FIG. 3C. As shown in FIG. 7D, the angle adjustment knob 55 includes access 53 for the terminal portion of the shaft 11 of an adapter block 6. In addition, the angle adjustment knob 55 can include an aperture 52 on one side of the knob 55 for a setscrew (not illustrated) that can lock the shaft 11 against the angle adjustment knob 55. The angle adjustment knob 55 can include an internal tension spring 56 that can compress the knob 55 against the shaft 11 of an adapter block 6 held in access 53. The angle adjustment knob 55 can also include a series of pegs 51 designed to fit into the indentations 34 of a slide block 4.

To rotate an adapter block 6 held by the angle adjustment knob 55, the knob 55 can be pulled upward as indicated by the directional arrow 54, which can compress the internal spring 56 and pull the pegs 51 out of the indentations 34 of a slide block 4. The knob 55 and associated adapter block 6 can then be rotated to the desired location. Upon release of the knob 55, the internal tension spring 56 can push the pegs 51 into the desired and mated indentations 34 of a slide block 4.

Figure 9:
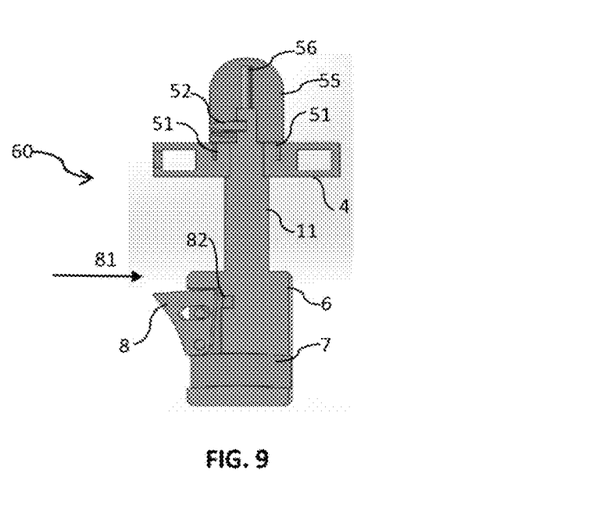
FIG. 9 illustrates a slider assembly of a positioning bracket.

FIG. 9 illustrates a slide block assembly 60 including an angle adjustment knob 55 that includes a series of pegs 51 following assembly with a slide block 4 and an adapter block 6. Of course, any suitable locking rotational device can be incorporated in a positioning bracket including, without limitation, a slotted collar system as illustrated in FIG. 3A, 3B, 3C; a ball and pin arrangement as further described below; or any other suitable design.

A positioning bracket can also include a drill guide lock that can provide for a bone tunnel drill guide to be secured in each adapter block. By way of example, and with reference to the slide block assembly of FIG. 9, an adapter block 6 can define a recess 7 and a locking block 8. In this particular embodiment, the locking block 8 can provide for a bone tunnel drill guide to be secured in the positioning bracket by use of a friction lock.

Figure 8A:
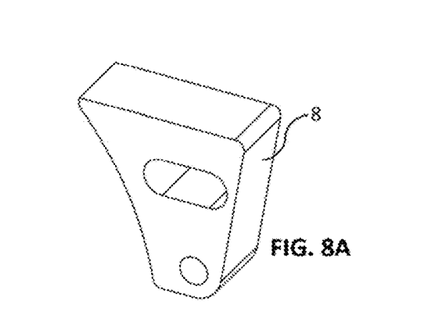
FIG. 8A illustrates a perspective view of a locking block.
Figure 8B:
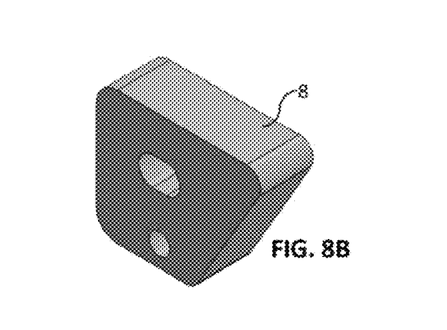
FIG. 8B illustrates a perspective view of another locking block.

FIG. 8A and FIG. 8B illustrate two embodiments of a locking block 8 for use in forming a friction lock between a bone tunnel drill guide and an adapter block of a positioning bracket. A locking block 8 can be retained in an adapter block 6 by use of pins, screws, etc. During use, the locking block 8 can be pushed in the direction indicated by the directional arrow 81 (FIG. 9). This can open the recess 7 and allow the end of a bone tunnel drill guide to be slid into the channel 7. Upon release of the locking block 8, a spring held in recess 82 can apply force between the lock block 8 and the drill guide to lock the drill guide into place.

A lock block 8 can exert suitable force on a drill guide so as to prevent release of the drill guide from the adapter block 6 during use. For instance, a lock block can secure a drill guide under a pulling force of about 40 N or more, for instance, from about 40 N to about 50 N.

Figure 10:
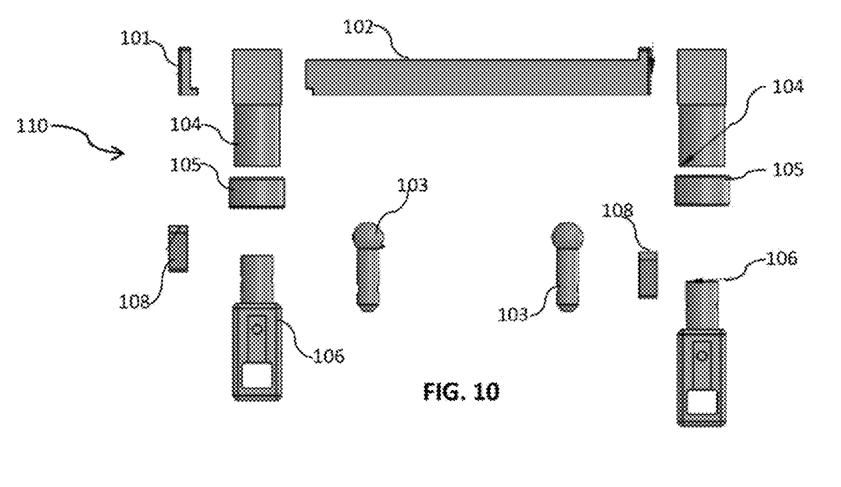
FIG. 10 illustrates an exploded view of another embodiment of a positioning bracket.
Figure 11A:
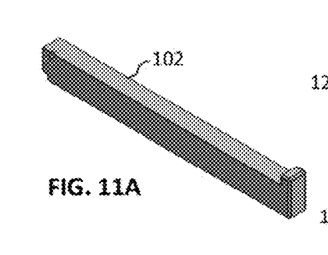
FIG. 11A illustrates a perspective view of a frame of a positioning bracket.
Figure 11B:
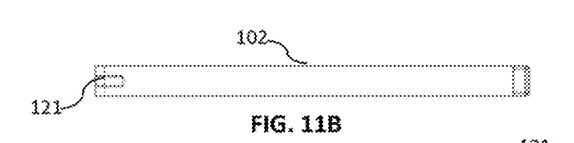
FIG. 11B is a first side view of a frame.
Figure 11C:
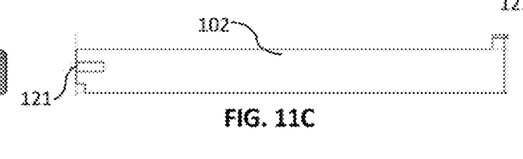
FIG. 11C is a second side view of a frame.
Figure 11D:
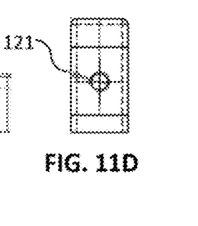
FIG. 11D is an end view of a frame.

FIG. 10 illustrates another embodiment of a positioning bracket 110 in an exploded view. The positioning bracket 110 includes a frame 102, a frame end 101, slide blocks 104, ball pin collars 105, ball pins 103, adapter blocks 106, and locking blocks 108. The various components of the positioning bracket 110 can be permanently or removably attached to one another via screws, welds, pins, etc. as are known in the art.

Figure 12A:
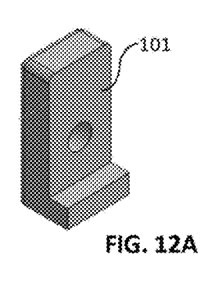
FIG. 12A is a perspective view of a frame end.
Figure 12B:
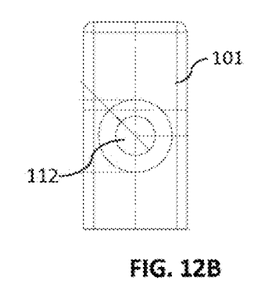
FIG. 12B is a first side view of a frame end.
Figure 12C:
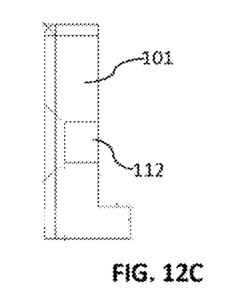
FIG. 12C is a second side view of a frame end.

FIGS. 11A, 11B, 11C, and 11D present various views of a frame 102. As illustrated, frame 102 is a single leg frame, rather than a rectangular double legged frame as discussed above. The frame 102 can be removably connectable to a frame end 101 as illustrated in FIGS. 12A, 12B, and 12C by an access 121. A setscrew or other locking device can hold the frame end 101 to the frame 102 via aperture 112 and access 121 according to standard methodology. Through utilization of a removable frame end 101, a slide block such as that illustrated in FIG. 13A-FIG. 13E can be removably attached to the frame 102.

Figures 13A, 13C:
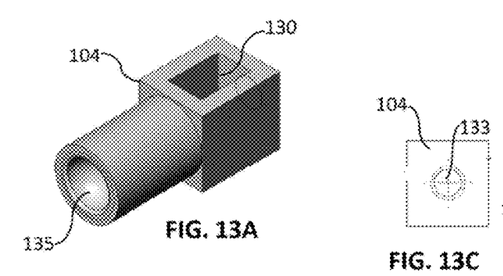
FIG. 13A illustrates a perspective view of a slide block of a positioning bracket.
FIG. 13C is a first end view of a slide block.
Figure 13B:
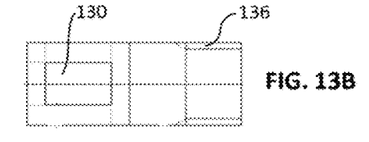
FIG. 13B is a side view of a slide block.
Figure 13D:
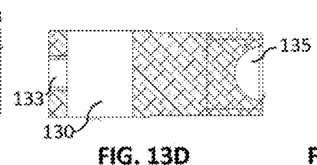
FIG. 13D is a sectional side view of a slide block.
Figure 13E:
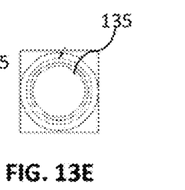
FIG. 13E is a second end view of a slide block.

The slide block 104 includes a channel 130 and a recess 135 and can be attached to the frame 102 via a single attachment rather than via multiple attachments as in a previously described embodiment. The slide block 104 can be located on frame 102 via the channel 130 and locked in place by use of a suitable locking mechanism, for instance by use of a setscrew held against the frame 102 via aperture 133 of the slide block 104.

Figure 14A:
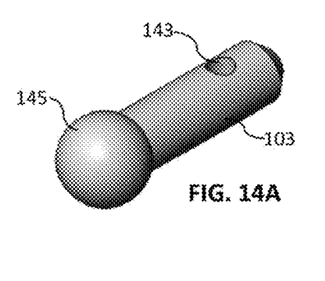
FIG. 14A illustrates a perspective view of a ball pin of a positioning bracket.
Figure 14B:
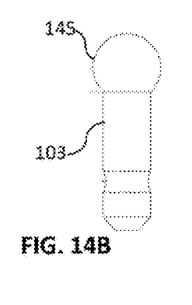
FIG. 14B is a first side view of a ball pin.
Figure 14C:
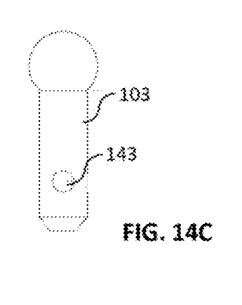
FIG. 14C is a second side view of a ball pin.
Figure 15A:
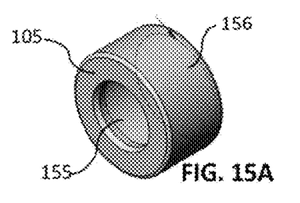
FIG. 15A illustrates a perspective view of a ball pin collar of a positioning bracket.
Figure 15B:
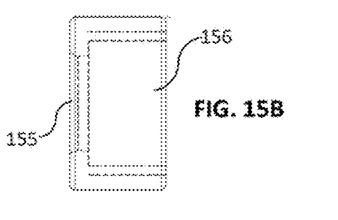
FIG. 15B is a side view of a ball pin collar.

The recess 135 of the slide block 104 is sized to mate with the ball 145 of a ball pin 103 as illustrated in FIGS. 14A, 14B, and 14C. The ball pin 143 includes the ball 145 at one end and an access 143 for securing the ball pin 103 to an adapter block. The ball pin 103 can be movably secured to the slide block 104 by use of a ball pin collar 105 as illustrated in FIGS. 15A and 15B. The ball pin collar 105 includes an aperture 155 that fits over the shaft of the ball pin 103 and an aperture 156 that fits over an end 136 of the slide block 104. Upon securement, the ball 145 of the ball pin 103 can be mated with the recess 135 of the slide block 104 in a fashion that can allow rotation of the ball pin 103 with multiple degrees of freedom. Upon location of the ball pin 103 at a desired angle and orientation with respect to the frame 102 and slide block 104, the ball pin can be secured in place, for instance by use of a set screw against the ball 145 or the like.

Figure 16A:
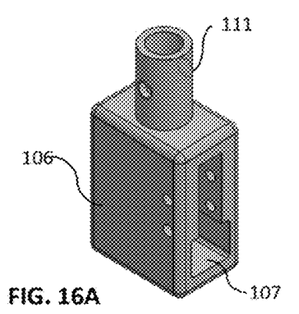
FIG. 16A illustrates a perspective view of an adapter block of a positioning bracket.
Figure 16B:
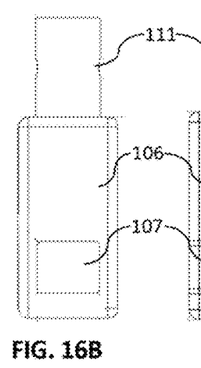
FIG. 16B is a first side view of an adapter block.
Figure 16C:
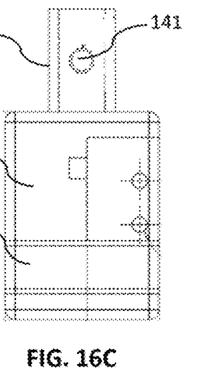
FIG. 16C is a second side view of an adapter block.
Figure 16D:
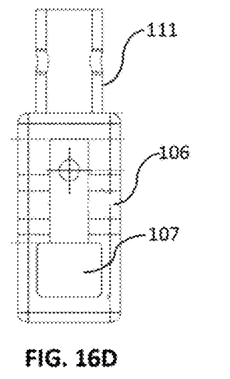
FIG. 16D is a third side view of an adapter block.

The second end of the ball pin 103 can include a recess 143 that can be used to lock the ball pin 103 to the shaft 111 of the adaptor block 106 as illustrated in FIG. 16A, FIG. 16B, FIG. 16C, and FIG. 16C. For instance a setscrew can be threaded through aperture 141 and tightened within access 143 thereby temporarily or permanently securing the adapter block 106 to the ball pin 103.

The aperture 106 can include a channel 107 for a drill guide end and can include a lock for securing the drill guide end within the channel 107. For instance, a locking block 8 as illustrated in FIG. 8A or FIG. 8B can be used to form a friction lock between the channel 7 of the adapter guide 106 and an end of a bone tunnel drill guide.

Figure 17A:
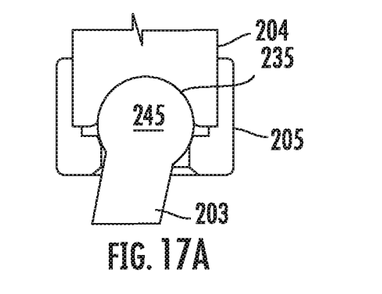
FIG. 17A is a cut-away view of a ball pin held with a slide block.

FIGS. 17A-17F illustrate another embodiment of a positioning bracket system. As seen in FIG. 17A, the positioning bracket can include a ball pin 203 and slide block 204 interconnection via the ball 245 of the ball pin 203 and the recess 235 of the slide block 204. The assembly can include a ball pin collar 205 that can connect the ball pin 203 to the slide block 204 while retaining motion capability of the ball pin 203 and hence the adapter block that can be connected to the slide pin 203.

Figure 17B:
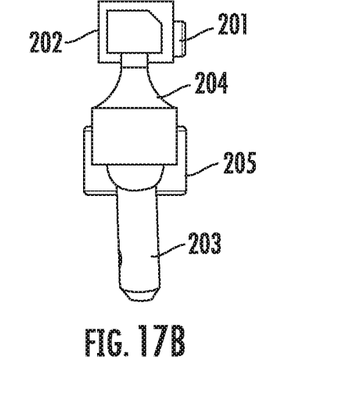
FIG. 17B illustrates an end view of a frame, slide block, and ball pin assembly.

FIG. 17B is an end view of an assembly including a frame 202, a slide block 204, a ball pin 203 and a ball pin collar 205. The assembly can include a lock screw 201 that can retain the slide block 204 in the frame 202. Upon tightening the lock screw 201, the slide block 204 can be held in the frame 202 and motion can be prevented. Upon loosening the lock screw 201, the slide block 204 can be slid across the frame 202 to a desired location.

Figure 17C:
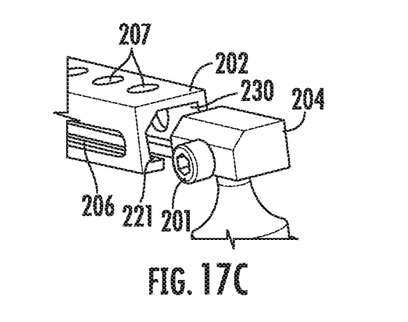
FIG. 17C illustrates a connection between a slide block and a frame.
Figure 17D:
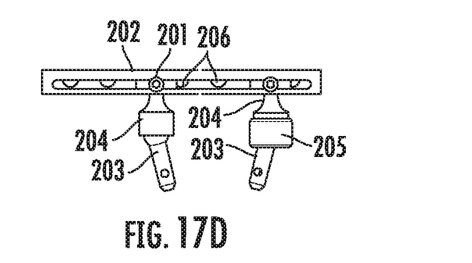
FIG. 17D illustrates a front view of a frame, slide block, and ball pin assembly.

FIG. 17C illustrates the single attachment interconnection between the frame 202 and the slide block 204. As can be seen, the frame 202 defines a channel 230 within which the body of the slide block 204 can fit. The channel 230 includes a track 221 that can support the slide block 204 and allow motion of the slide block 204 laterally across the frame 202. The frame 202 defines a lateral aperture 206. Upon location of the slide block 204 within the channel 230 and supported by the track 221, the lock screw 201 can be inserted through the lateral aperture 206 and into a properly sized receiving access of the slide block. Thus, and as illustrated in FIG. 17D, upon moving the slide block 204 to the desired position in the frame 202, the lock screw 201 can be tightened against the frame 202 and the slide block 204 to secure the slide block 204 at the desired location.

Figure 17E:
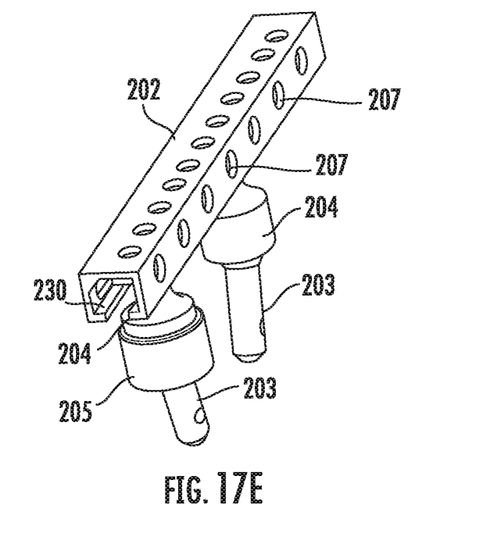
FIG. 17E illustrates a perspective view of a frame, slide block, and ball pin assembly.
Figure 17F:
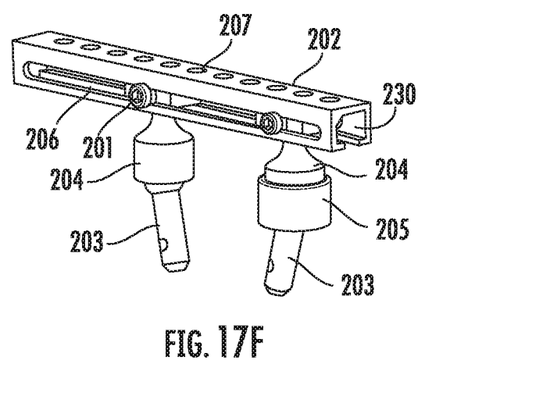
FIG. 17F illustrates a perspective view of a frame, slide block, and ball pin assembly.

FIG. 17E and FIG. 17F illustrate two different perspectives of this assembly showing the ball pin 203 attached to the slide block 204 via the ball pin collar 205. Also shown is the slide block 204 retained in the channel 230 of the frame 202 via the lock screw 201 and in a slidable fashion along the lateral aperture 206 of the frame 202.

An assembly can also include apertures 207 in the frame 202. Such apertures can decrease the weight of the positioning bracket and can also decrease the material requirements of formation of the bracket, which can decrease costs and ensure ease of use.

In utilization of a positioning bracket, the arm of a first drill guide can be inserted into a first adapter block of the device and the arm of a second drill guide can be inserted into a second adapter block of the device. Following, surgeon can locate the drill guides as desired with respect to one another and to the patient by use of the adjustable slide blocks and any rotational components.

Figure 18:
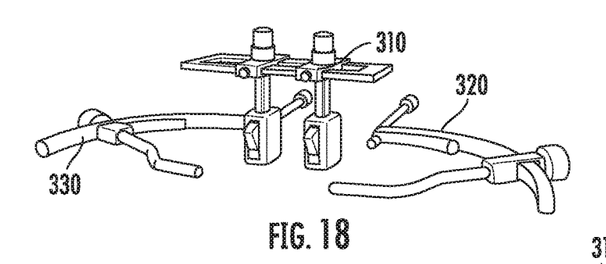
FIG. 18 illustrates a positioning bracket and two bone tunnel drill guides.
Figure 19:
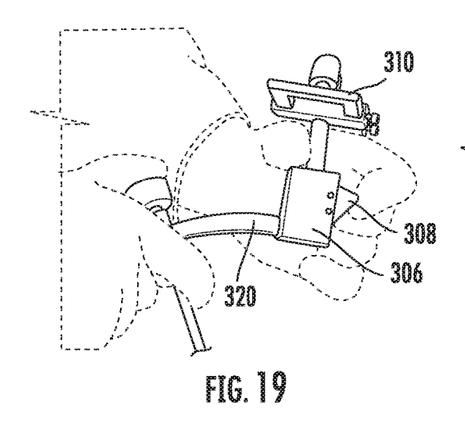
FIG. 19 illustrates the attachment of a first bone tunnel drill guide to a positioning bracket.

By way of example, FIG. 18 illustrates a positioning bracket 310 and bone tunnel drill guides 320, 330 that can be secured by the positioning bracket 310. As illustrated in FIG. 19, a first drill guide 320 can be secured to the positioning bracket 310 by locating the end of the handle of the drill guide 320 within the channel of the adapter block 306 and locking it in place by use of the locking block 308. The drill guide 320 can be secured to the positioning bracket 310 in such a fashion that the securement does not interfere with the guide arm of the drill guide, as shown.

Figure 20:
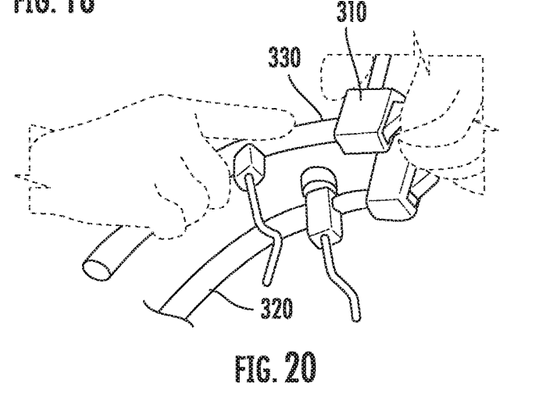
FIG. 20 illustrates the attachment of a second bone tunnel drill guide to a positioning bracket.
Figure 21:
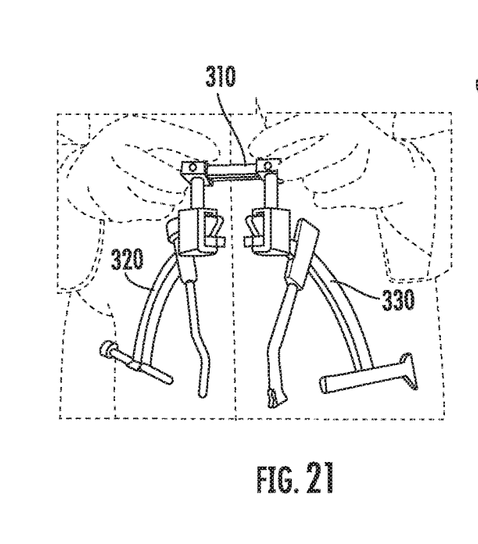
FIG. 21 illustrates a positioning bracket assembled with two bone tunnel drill guides.
Figure 22:
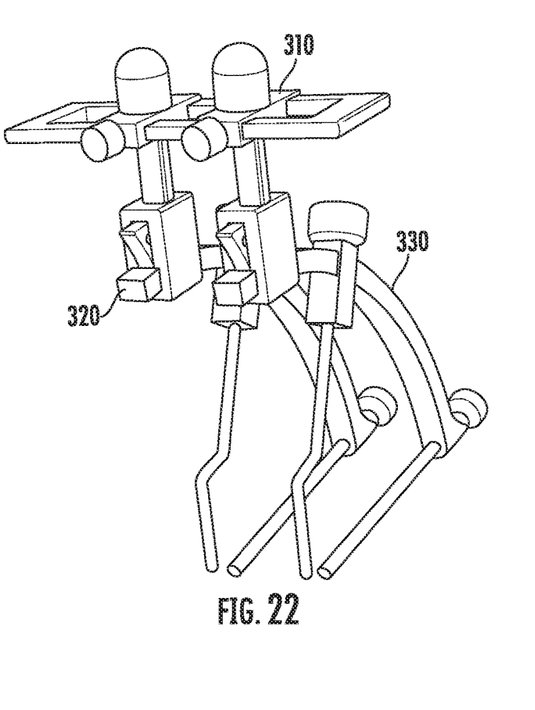
FIG. 22 illustrates a positioning bracket assembled with two bone tunnel drill guides.

The second drill guide 330 can likewise be secured to the positioning bracket 310 by use of the second adaptor block of the positioning bracket (FIG. 20). The handles of the drill guides 320, 330 can slide into the respective channels of the adapter blocks 306 when the locking blocks 308 are depressed. Once the locking block 308 is released, the drill guide 320, 330 is locked in place due to the force generated by an internal spring. FIG. 21 and FIG. 22 illustrated a system following assembly.

Following assembly, the system can withstand forces expected to be encountered during surgery without detrimentally affecting surgical accuracy. For instance, the various locking mechanisms (e.g., friction and screw locks) can avoid slip under clinically relevant loading regimes (e.g., about 50 N).

Positioning brackets can be ergonomically designed so as to ensure that the assembled system can be held throughout a surgery without inducing fatigue or affecting tunnel placement accuracy. Accordingly, the disclosed positioning brackets can provide improvement in surgical efficiency and a decrease in operating time in comparison with single device systems currently being used.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A positioning bracket comprising:
a frame;
a first slide block attached to the frame, the first slide block being capable of motion in a lateral direction across the frame, the first slide block including a first locking mechanism that is engagable with the frame to secure the first slide block at a first securement location;
a second slide block attached to the frame, the second slide block being capable of motion in the lateral direction across the frame, the second slide block including a second locking mechanism that is engagable with the frame to secure the second slide block at a second securement location;
a first adapter block attachable to the frame via the first slide block, the first adapter block being configured to secure a first bone tunnel drill guide, the first adapter block being rotatable about a first axis that passes through the first slide block when the positioning bracket is fully assembled;
a third locking mechanism configured to lock the first adapter block at a first angle of rotation with respect to the first slide block;
a second adapter block attachable to the frame via the second slide block, the second adapter block being configured to secure a second bone tunnel drill guide, the second adapter block being rotatable about a second axis that passes through the second slide block when the positioning bracket is fully assembled; and
a fourth locking mechanism configured to lock the second adapter block at a second angle of rotation with respect to the second slide block.

2. The positioning bracket of claim 1, wherein the first adaptor block is rotatable about a third axis.

3. The positioning bracket of claim 2, wherein the second adaptor block is rotatable about a fourth axis.

4. The positioning bracket of claim 1, wherein the first locking mechanism that is engagable with the frame comprises a compression locking mechanism.

5. The positioning bracket of claim 4, wherein the second locking mechanism that is engagable with the frame comprises a compression locking mechanism.

6. The positioning bracket of claim 1, wherein the first adaptor block is configured to secure a bone tunnel drill guide via a friction locking mechanism.

7. The positioning bracket of claim 6, wherein the second adaptor block is configured to secure a bone tunnel drill guide via a friction locking mechanism.

8. A method for locating multiple bone tunnel drill guides on the positioning bracket of claim 1 comprising:
- securing a first bone tunnel drill guide to the first adapter block of the positioning bracket;
- securing a second bone tunnel drill guide to the second adapter block of the positioning bracket;
- moving the first slide block and the second slide block of the positioning bracket laterally with respect to one another along the frame of the positioning bracket, the first and second slide blocks being attached to the first and second adapter blocks, respectively;
- locking the first and second slide blocks to the frame.

9. The method of claim 8, further comprising rotating the first and second adapter blocks with respect to the first and second slide blocks, respectively, and locking the adapter blocks in place by use of the third and fourth locking mechanisms.

10. The method of claim 9, further comprising rotating the first and second bone tunnel drill guides with respect to one another and locking the first and second bone tunnel drill guides in place at a predetermined relationship to one another.

11. The method of claim 8, wherein the first and second bone tunnel drill guides are secured to the first and second adapter blocks by a friction lock.

12. The positioning bracket of claim 1, wherein the first and second slide blocks are removably attachable to the first and second adapter blocks.

13. The positioning bracket of claim 1, the first and second slide blocks each further comprising positional markings at angular increments of about 5° or less located with respect to the third and fourth locking mechanisms, respectively, for identifying the first and second angles of rotation.

14. The positioning bracket of claim 1, wherein the frame exhibits bending of about 0.1 millimeter or less under a force of 11 Newtons.

15. The positioning bracket of claim 1, the first adapter block comprising a first shaft that passes through the first slide block along the first axis and the second adapter block comprising a second shaft that passes through the second slide block along the second axis, wherein each of the first shaft and the second shaft exhibit negligible deflection under a force of 50 Newtons.

16. The positioning bracket of claim 1, further comprising the first bone tunnel drill guide and the second bone tunnel drill guide.

17. The positioning bracket of claim 16, wherein upon securing the first and second bone tunnel drill guides, the first adapter block and the second adapter block each prevent release of the respective first and second bone tunnel drill guide under a pulling force of about 50 Newtons.

* * * * *